United States Patent [19]

Bermes

[11] Patent Number: 5,770,708
[45] Date of Patent: Jun. 23, 1998

[54] PREPARATION OF PHENYLAZONAPHTHALENES

[75] Inventor: Rudolf Bermes, Ludwigshafen, Germany

[73] Assignee: BASF Aktiengesellschaft, Ludwigshafen, Germany

[21] Appl. No.: 863,195

[22] Filed: May 27, 1997

[30] Foreign Application Priority Data

May 31, 1996 [DE] Germany ............... 196 21 840.3

[51] Int. Cl.⁶ ............... C09B 41/00; C09B 67/26
[52] U.S. Cl. ............... 534/581; 534/728; 534/882; 8/527
[58] Field of Search ............... 534/581, 728, 534/882; 8/527

[56] References Cited

U.S. PATENT DOCUMENTS

| | | | |
|---|---|---|---|
| 3,792,077 | 2/1974 | Bermes et al. | 558/488 |
| 4,035,350 | 7/1977 | Landler et al. | 534/882 X |
| 4,058,517 | 11/1977 | Bermes | 534/581 |
| 5,173,086 | 12/1992 | Bermes | 8/527 |

FOREIGN PATENT DOCUMENTS

| | | |
|---|---|---|
| 889 088 | 12/1981 | Belgium . |
| 2 209 478 | 9/1973 | Germany . |
| 2079771 | 1/1982 | United Kingdom . |

*Primary Examiner*—Fiona T. Powers
*Attorney, Agent, or Firm*—Oblon, Spivak, McClelland, Maier & Neustadt, P.C.

[57] ABSTRACT

A process for preparing aqueous preparations of azo dyes of the formula

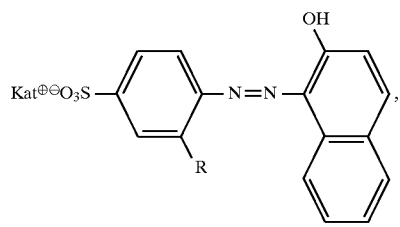

where

R is hydrogen or $C_1$–$C_4$-alkyl and

Kat⊕ is the equivalent of a cation which derives from a tertiary amine of the ethanolamine or propanolamine series, by diazotization of an aniline of the formula

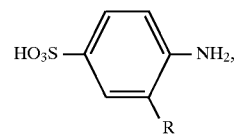

with neopentylglycol dinitrite in an aqueous medium and coupling of the resulting reaction mixture with β-naphthol in the presence of a water-miscible diluent and of an amine comprises using an amine comprising a tertiary amine of the ethanolamine or propanolamine series.

4 Claims, No Drawings

PREPARATION OF PHENYLAZONAPHTHALENES

The present invention relates to a novel process for preparing certain phenylazonaphthalenes by diazotization of anilinesulfonic acids by means of neopentylglycol dinitrite in an aqueous medium and coupling of the resulting reaction mixture onto β-naphthol in the presence of a water-miscible diluent and of an amine.

DE-A-2 209 478 discloses the preparation of the dye C.I. Acid Orange 7 (15 510) starting from 4-aminobenzenesulfonic acid and β-naphthol. However, the method of preparation described therein affords the dye solutions in an unsatisfactory yield. What is more, the resulting dye solutions additionally comprise volatile amines in some instances.

BE-A-889 088 describes the diazotization of sulfanilic acid with alkali metal nitrite and sulfuric acid in a low-water medium. The coupling with β-naphthol takes place in the presence of technical grade triethanolamine. However, the yield of dye thus prepared is unsatisfactory.

It is an object of the present invention to provide a novel process for preparing aqueous preparations of C.I. Acid Orange 7 and similar dyes without the abovementioned disadvantages.

We have found that this object is achieved by a process for preparing aqueous preparations of azo dyes of the formula I

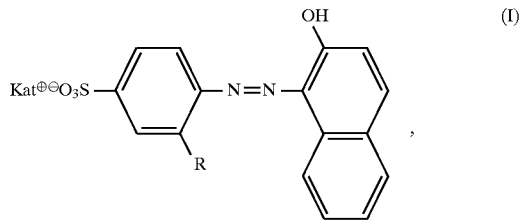

where
R is hydrogen or $C_1$–$C_4$-alkyl and
Kat⊕ is the equivalent of a cation which derives from a tertiary amine of the ethanolamine or propanolamine series, by diazotization of an aniline of the formula II

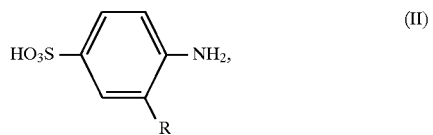

where R is as defined above, with neopentylglycol dinitrite in an aqueous medium, preferably in an aqueous medium which is essentially free of organic solvents, and coupling of the resulting reaction mixture with β-naphthol in the presence of a water-miscible diluent and of an amine, which comprises using an amine comprising a tertiary amine of the ethanolamine or propanolamine series.

R is for example methyl, ethyl, propyl, isopropyl, butyl, isobutyl, sec-butyl or tert-butyl.

The preparation of dyes of the formula I where R is hydrogen or methyl is preferred, methyl being particularly preferred.

Suitable amines of the ethanolamine or propanolamine series include for example N,N-di-($C_1$–$C_4$-alkyl)-ethanolamines, -propanolamines or -isopropanolamines, such as N,N-dimethyl-ethanolamine, -propanolamine or -isopropanolamine, N,N-diethyl-ethanolamine, -propanolamine or -isopropanolamine, N,N-dipropyl-ethanolamine, -propanolamine or -isopropanolamine, N,N-diisopropyl-ethanolamine, -propanolamine or -isopropanolamine or N,N-dibutylethanolamine, -propanolamine or -isopropanolamine, N-($C_1$–$C_4$-alkyl)-diethanolamines, -dipropanolamines or -diisopropanolamines, such as N-methyl-diethanolamine, -dipropanolamine or -diisopropanolamine, N-ethyl-diethanolamine, -dipropanolamine or -diisopropanolamine, N-propyl-diethanolamine, -dipropanolamine or -diisopropanolamine, N-isopropyl-diethanolamine, -dipropanolamine or -diisopropanolamine, or N-butyl-diethanolamine, -dipropanolamine or -diisopropanolamine, -triethanolamine, -tripropanolamine, -triisopropanolamine, N-(2-hydroxyethyl)pyrrolidine, N-(2- or 3-hydroxypropyl)pyrrolidine, N-(2-hydroxylethyl)piperidine, N-(2- or 3-hydroxypropyl)piperidine, N-(2-hydroxyethyl)morpholine, N-(2- or 3-hydroxypropyl)morpholine or N,N-dimethyl- or N,N-di-ethyl-N-(5-hydroxy-3-oxapentyl)amine.

Particularly suitable amines are triethanolamine, N-($C_1$–$C_4$-alkyl)diethanolamines, N,N-di($C_1$–$C_4$-alkyl) ethanolamines, N,N-dimethylpropanolamine and mixtures thereof.

The use of N,N-diethylethanolamine is particularly preferred.

Suitable water-miscible diluents include for example glycols, such as 1,2-propanediol, 1,3-propanediol, 1,2-butanediol, 2,3-butanediol, 1,4-butanediol, 1,2-pentanediol, 2,3-pentanediol, 1,5-pentanediol and 2,2-dimethyl-1,3-propanediol (neopentylglycol), $C_1$–$C_4$-monoalkyl ethers of mono- or diglycols, such as 2-methoxyethanol, 2-ethoxyethanol, 2-propoxyethanol, 2-butoxyethanol, 1-methoxypropan-2-ol, 1-ethoxypropan-2-ol, 3-methoxypropanol, 3-ethoxypropanol, 4-methoxybutanol, 4-ethoxybutanol, diethylene glycol monomethyl, monoethyl, monopropyl or monobutyl ether or dipropylene glycol monomethyl, monoethyl, monopropyl or monobutyl ether, di-, tri- or tetraglycols, such as diethylene glycol, triethylene glycol, tetraethylene glycol, dipropylene glycol, tripropylene glycol or tetrapropylene glycol, cyclic carboxylic esters, such as γ-butyrolactone, or cyclic carboxamides, such as pyrrolidone, N-methyl- or N-ethyl-pyrrolidone or ε-caprolactam.

The use of di- or triethylene glycol or di- or tripropylene glycol as water-miscible solvent is preferred, dipropylene glycol being particularly preferred.

The neopentylglycol dinitrite, which is known and described for example in U.S. Pat. No. 37 92 077, is generally used in an amount of from 0.5 to 0.56 mol, preferably from 0.5 to 0.53 mol, per mole of aniline II.

The β-naphthol is generally used in an amount of from 1.0 to 1.1 mol, preferably from 1.02 to 1.05 mol, per 1 mol of aniline II.

The tertiary amine of the ethanolamine or propanolamine series is preferably used in the coupling in an amount of from 1.0 to 1.15 mol, in particular from 1.05 to 1.1 mol, per 1 mol of β-naphthol.

The β-naphthol is preferably used in a mixture with from 30 to 50% by weight of water and from 45 to 70% by weight of a water-miscible diluent, based on the weight of β-naphthol in the coupling reaction.

The abovementioned limits are not binding. It is possible to use other weight ratios. The primary consideration is that the β-naphthol reactant be in solution.

The diazonium salt is prepared in a conventional manner at from 5° to 35° C., preferably from 25° to 30° C., at atmospheric pressure.

The coupling reaction generally takes place at from 5° to 500° C., preferably at from 25° to 350° C., likewise at atmospheric pressure.

The process of this invention is advantageously carried out by charging a suitable apparatus, for example a stirred apparatus, initially with a mixture of water and aniline II and metering the neopentylglycol dinitrite in at the abovementioned temperature. The diazotization will generally have ended after 2–4 hours of subsequent stirring.

Separately, a mixture of water, β-naphthol, diluent and tertiary amine is prepared in another stirred apparatus and adjusted to the abovementioned temperature. Thereafter the reaction mixture of the diazotization reaction is metered in. Following a subsequent stirring period of generally from 15 to 60 minutes, the reaction will have ended. The resulting solution, if necessary after a clarifying filtration and adjustment to the desired color strength, is directly ready-to-use.

It is advantageously useful for dyeing or printing polymeric material, especially paper stock, but also cellulose, cotton, leather, baste fibers, hemp, flax, sisal, jute, coir or straw.

The process of this invention affords the azo dyes of the formula I in a high yield. They are obtained directly as an aqueous solution with a neutral pH, i.e. a pH within the range from about 7 to 8.

The Example which follows illustrates the invention.

EXAMPLE a) 177 g of 2-methylaniline-4-sulfonic acid and 9.5 g of aniline-4-sulfonic acid were presented in 600 ml of water. To this mixture were added 85.5 g of neopentylglycol dinitrite at 25°–30° C. over 40 min with stirring. The batch was subsequently stirred at 25°–30° C. for 2 h and excess nitrite was then destroyed with 0.5 g of sulfamic acid and the reaction mixture was cooled down to 10° C.

b) 60 ml of water, 85 g of dipropylene glycol, 126 g of N,N-di-ethylethanolamine and 147 g of β-naphthol were introduced into a flask and stirred for 1 h. The resulting solution was cooled down to 20° C., and the mixture described under a) was added over 30 min with stirring. A little further N,N-diethylethanolamine was added to the reaction mixture until the reaction mixture pH was within the range from 7 to 7.5. At this point the reaction was complete.

40 ml of water and 3 g of diatomite were added and the reaction mixture was filtered through a clarifying filter, affording 1430 g of an aqueous solution comprising 432 g of the dye of the formula

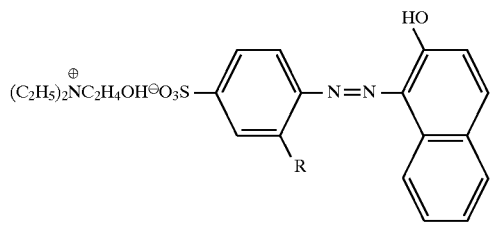

(R=CH$_3$) and 26 g of the dye of the abovementioned formula (R=H).

EXAMPLES 2 to 5

The N,N-diethylethanolamine in Example 1b was replaced by
186 g of N,N-dibutylethanolamine (Example 2)
112 g of N,N-dimethylisopropanolamine (Example 3)
143 g of N,N-dimethyl-N-(5-hydroxy-3-oxapentyl)amine (Example 4)
141 g of N-(2-hydroxyethyl)morpholine (Example 5)
174 g of N-butyldiethanolamine (Example 6)
and similar results were obtained in each case.

EXAMPLE 7 a) 173 g of 4-aminobenzenesulfonic acid were presented in 550 ml of water and mixed with 85.5 g of neopentylglycol dinitrite at 25°–30° C. with stirring. The mixture was subsequently stirred at 28°–30° C. for 2 h, the remaining nitrite was destroyed with 0.8 g of sulfamic acid, and the suspension was cooled down to 8° C.

b) 147 g of β-naphthol were dissolved in a mixture of 85 g of dipropylene glycol, 126 g of N,N-diethylethanolamine and 60 ml of water. The mixture described under a) was gradually added with stirring while the temperature was adjusted to 20°–30° C. by cooling. The pH was finally adjusted to 7.4 with 1.6 g of N,N-diethylethanolamine. Following addition of 3 g of diatomite and 100 ml of water a clarifying filtration afforded 1334 g of a solution comprising 445 g of the dye of Example 1 (R=H; C.I. Acid Orange 7).

EXAMPLE 8

187 g of 2-methylaniline-4-sulfonic acid were diazotized in the manner of Example 1a) and coupled with β-naphthol in the manner of Example 1b), affording 1430 g of a solution comprising 459 g of the dye of Example 1 (R=CH$_3$; C.I. Acid Orange 8).

EXAMPLES 9 to 15

The dipropylene glycol used in Example 8 was replaced by equal amounts of
diethylene glycol (Example 9)
triethylene glycol (Example 10)
1,4-butanediol (Example 11)
1,5-pentanediol (Example 12)
neopentylglycol (Example 13)
1-methoxy-2-propanol (Example 14)
diethylene glycol monobutyl ether (Example 15)
and similar concentrated solutions of C.I. Acid Orange 8 were obtained in each case.

I claim:

1. A process for preparing aqueous preparations of azo dyes of the formula I

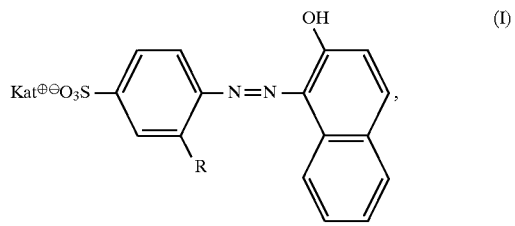

where

R is hydrogen or C$_1$–C$_4$-alkyl and

Kat⊕ is the equivalent of a cation which derives from a tertiary amine of the ethanolamine or propanolamine series, by diazotization of an aniline of the formula II

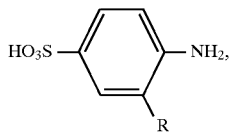

(II)

where R is as defined above, with neopentylglycol dinitrite in an aqueous medium and coupling of the resulting reaction mixture with β-naphthol in the presence of a water-miscible diluent and of an amine, which comprises using an amine comprising a tertiary amine of the ethanolamine or propanolamine series.

2. A process as claimed in claim 1, wherein R is hydrogen or methyl.

3. A process as claimed in claim 1, wherein the tertiary amine used is triethanolamine, N-($C_1$–$C_4$-alkyl)diethanolamine, N,N-di($C_1$–$C_4$-alkyl)ethanolamine, N,N-dimethylpropanolamine or a mixture thereof.

4. A process as claimed in claim 1, wherein the tertiary amine used is N,N-diethylethanolamine.

* * * * *